(12) United States Patent
Hiereth et al.

(10) Patent No.: US 10,258,410 B2
(45) Date of Patent: Apr. 16, 2019

(54) METHOD FOR GENERATING SHAPED LASER PULSES IN A LITHOTRIPTER AND A LITHOTRIPTER

(71) Applicants: Werner Hiereth, Gilching (DE); Detlef Russ, Renningen (DE); Stefan Biggel, Mittenwald (DE); Raimund Hibst, Erbach (DE)

(72) Inventors: Werner Hiereth, Gilching (DE); Detlef Russ, Renningen (DE); Stefan Biggel, Mittenwald (DE); Raimund Hibst, Erbach (DE)

(73) Assignee: DORNIER MEDTECH LASER GMBH, Wessling (DE)

(*) Notice: Subject to any disclaimer, the term of this patent is extended or adjusted under 35 U.S.C. 154(b) by 694 days.

(21) Appl. No.: 14/523,612

(22) Filed: Oct. 24, 2014

(65) Prior Publication Data

US 2015/0100048 A1 Apr. 9, 2015

Related U.S. Application Data

(63) Continuation of application No. PCT/EP2012/001805, filed on Apr. 26, 2012.

(51) Int. Cl.
*A61B 18/26* (2006.01)
*A61B 17/00* (2006.01)
*A61B 18/00* (2006.01)

(52) U.S. Cl.
CPC .... *A61B 18/26* (2013.01); *A61B 2017/00159* (2013.01); *A61B 2018/00702* (2013.01); *A61B 2018/00779* (2013.01)

(58) Field of Classification Search
CPC .................. A61B 18/26; A61B 2017/00159
(Continued)

(56) References Cited

U.S. PATENT DOCUMENTS

| | | | |
|---|---|---|---|
| 4,939,336 A | * | 7/1990 | Meyer .................. A61B 18/20 |
| | | | 219/121.62 |
| 5,009,658 A | | 4/1991 | Damgaard-Iversen et al. |

(Continued)

FOREIGN PATENT DOCUMENTS

| | | |
|---|---|---|
| DE | 10230626 | 1/2004 |
| RU | 2272660 | 3/1996 |

(Continued)

OTHER PUBLICATIONS

Russian Search Report for RU 2014138726 accompanying below Office Action.

(Continued)

*Primary Examiner* — Niketa I Patel
*Assistant Examiner* — Nathan A Baldwin
(74) *Attorney, Agent, or Firm* — King & Spalding LLP

(57) ABSTRACT

Method for generating a shaped laser pulse in a lithotripter characterized in that if the pulse duration is divided into four intervals of equal length, less than 25% of the energy of the pulse is emitted in the first of those intervals, and in that the maximum intensity of the pulse is first reached in the second, third or fourth time interval, and wherein the intensity reached after the start of the third and/or forth interval is at least once the same as or higher than the maximum intensity reached in the second interval.

7 Claims, 2 Drawing Sheets

(58) Field of Classification Search
USPC .......................................................... 606/2.5
See application file for complete search history.

(56) References Cited

U.S. PATENT DOCUMENTS

| | | | | |
|---|---|---|---|---|
| 5,059,200 | A * | 10/1991 | Tulip | A61B 18/26 606/2.5 |
| 5,269,778 | A * | 12/1993 | Rink | A61B 18/20 606/12 |
| 5,820,627 | A * | 10/1998 | Rosen | A61B 18/26 606/12 |
| 6,538,739 | B1 * | 3/2003 | Visuri | A61B 18/26 356/388 |

FOREIGN PATENT DOCUMENTS

| | | |
|---|---|---|
| RU | 2318466 | 3/2008 |
| WO | WO 89/10647 | 11/1989 |
| WO | WO 90/12544 | 11/1990 |
| WO | WO 94/23478 | 10/1994 |
| WO | WO 08/024022 | 2/2008 |

OTHER PUBLICATIONS

Russian Office Action dated Mar. 16, 2016 in Russian with English translation.

International Search Report for PCT/EP2012/001805, dated Apr. 9, 2012.

"Recoil momentum at a solid surface during developed laser ablation" (Quantum Electron 1993; 23;1035-1038 by Kuznetsov.

"Comparison of the effects of absorption coefficient and pulse duration of 2,12 µm and 2.79 µm radiation on ablation of tissue" IEEE J Quantum Electron 1996; 32 :2025-2036 by Frenz M, Prati.so H, Konu F, et al).

"Noncontact tissue ablation by holmium YSGG laser pulses in blood" (Laser Surg. Med.. 1991;'11:26-34 by Van Leeuwen TG, van der Veen M. Verdaasdonk RM, Borst C.).

"Transient cavities near boundaries" (J. Fluid Mech 1986; 110:419-419 by Blake .JR, Taib 86, Doherty G.

Dependence of Calculus Retropulsion on Pulse Duration During Ho: YAG Laser Lithotripsy by Kang HW; Lasers in Surgery and Medicine 38:762-772 (2006).

* cited by examiner

METHOD FOR GENERATING SHAPED LASER PULSES IN A LITHOTRIPTER AND A LITHOTRIPTER

RELATED APPLICATIONS

The present application is a continuation of and claims priority to PCT application PCT/EP2012/001805, filed Apr. 26, 2012, and titled "A Method For Generating Shaped Laser Pulses In A Lithotripter And A Lithotripter," the content of which is incorporated herein in its entirety.

TECHNICAL FIELD

This invention relates to a method for generating pulses with a certain shape in a lithotripter and a lithotripter. Such pulses can e.g. be generated using a pulsed pumped solid state laser. In addition, the invention also relates to methods of using the above mentioned method, the described pulse and/or the above mentioned lithotripter for lithotripsy.

BACKGROUND

The mechanism of stone fragmentation with a pulsed solid state laser is known in the field of lithotripsy. The primary mechanism when using infra-red lasers in lithotripsy is usually of a photo thermal nature, wherein the thermal destruction of the stone composition with direct light absorption and minimal pressure waves is the predominant effect. For a maximum effect the laser fiber needs to be contact or close to the calculus which should be treated. A typical laser pulse of a flash lamp pumped solid state laser, which is conventionally used in the field of lithotripsy, usually creates a large, fast circular growing vapor bubble. While this growing vapor bubble has not reached the stone, energy from the pulse is still absorbed in the water. Once the vapor bubble has met the stone, the energy emitted by the pulse after that event is in the best case not absorbed by water before it reaches the stone and can completely be absorbed by the calculus. When the vapor bubble collapses the stone is moved away from the fiber tip due to the Kelvin Impulse. In addition, the calculus also moves due to the ablation plume ejected because of the conservation of the momentum. The expressions calculus and stone are used interchangeably in this text.

It is shown e.g. in "Dependence of Calculus Retropulsion on Pulse Duration During Ho:YAG Laser Lithotripsy" by Kang HW, et al. that the retropulsion could be reduced by applying pulses with lower amplitude, but longer pulse times. However, Kang also showed that the longer pulses reduce the ablation volume.

As described before, in many state of the art methods only a small part of the pulse energy is used for the stone disintegration. According to the state of the art in some cases the retropulsion is reduced while also reducing the ablation efficiency.

Further documents of the background for this invention comprise the document U.S. Pat. No. 5,820,627 by Rosen et al. disclosing real time optical feedback control of laser lithotripsy, wherein the laser pulse parameters are adjusted according to measured incandescent photoemissions emitted for irradiated biological material. The laser pulses are directed to a target area of the subject using a delivery system.

In the document WO 94/23478 titled "Q-switched laser system, in particular for laser lithotripsy" by Muller et al. a Q-switched laser system is described which has a laser active medium in a resonator, an optical pumping arrangement and a passive Q-switch. In addition, a resonator extension having an optical wave guide is associated to the laser-active medium in order to increase the laser pulse length.

Document WO 89/10647 discloses a device for generating laser pulses of variable duration. It discloses a device comprising a resonator in which a first continuously pumped neodymium-YAG (Nd:YAG) crystal and a switchable optical seal which functions as a Q-switch are arranged. To increase the pulse power in the beam path of the continuous-wave Nd:YAG laser, a second Nd:YAG crystal which is pumped in pulses is arranged after the resonator and outside the seal.

Further information about the background of this invention can be found for example in "Recoil momentum at a solid surface during developed laser ablation" (Quantum Electron 1993; 23:1035-1038 by Kuznetsov LI) as well as in "Comparison of the effects of absorption coefficient and pulse duration of 2.12 µm and 2.79 µm radiation on ablation of tissue" (IEEE J Quantum Electron 1996;32:2025-2036 by Frenz M, Pratiso H, Konu F, et al.). Further background documents include "Non contact tissue ablation by holmium YSGG laser pulses in blood" (Laser Surg. Med. 1991;11: 26-34 by Van Leeuwen TG, van der Veen MJ, Verdaasdonk RM, Borst C.). Additional information can also be found in "Transient cavities near boundaries" (J Fluid Mech. 1986; 170:479-479 by Blake JR, Taib BB, Doherty G.).

Document WO 2008/024 022 A1 discloses a laser device based on two laser emitters. Document RU 2 272 660 C2 discloses a method of treating patients suffering from nepholythiasis.

Starting from this background, this invention addresses the problem of generating laser pulses which can then be used e.g. to increase the efficiency in methods and systems usable in lithotripsy. The invention is therefore also related to the question of how to generally improve a treatment method and system used for lithotripsy. The invention provides a method according to claim 1 and a lithotripter according to claim 9. Preferred embodiments are disclosed in the dependent claims.

SUMMARY

A pulse shaped in a lithotripter according to a method according to the invention may be characterized in that if the pulse duration is divided into four (time) intervals I1, I2, I3, and I4, of equal lengths, a pulse shaped according to the method of the invention emits less than 25% of the total energy of the whole pulse in the first of those intervals I1, I2, I3, and I4. In addition, the maximum intensity of the pulse is reached for the first time in the second time interval I2, third time interval I3 and/or fourth time interval I4. In particular, it may not be reached in the first time interval I1. Furthermore, the intensity reached after the start of the third interval I3 and/or fourth interval I4 is at least once the same as or higher than the maximum intensity reached in the second interval I2. In particular, the maximum intensity of the pulse may e.g. be reached in the second time interval I2 and remain constant at the maximum intensity of the pulse during the third interval I3 and in some cases also part of the fourth interval I4. In other examples the maximum intensity of the pulse may only be reached in the third interval I3 and/or fourth interval I4. The expression "at least once" may mean that at least at one time the described intensity is reached.

In particular, in the first interval of the four intervals of equal lengths in which the pulse duration is divided, less than 25%, in particular less than 20%, in particular less than 15% and in particular less than 10%, in particular less than 5% of the complete (total) energy of the pulse may be emitted. State of the art pulses may emit in the first of four intervals of equal lengths more than 25% or even more than 30% or more of the complete (total) energy of the pulse. In this text, the start of a pulse may be defined as the time when the pulse has reached 10% of its maximum (intensity) amplitude. Accordingly, its end may be defined as the time after the maximum amplitude has been reached when the pulse has decreased to 10% of its maximum (intensity) amplitude.

When the expressions "intervals" or "time intervals" are used in this text the expressions may refer to (time) intervals of equal lengths and/or to (time) intervals of non-equal lengths. The expression "time window" or "window" may refer to (time) windows of equal or non equal lengths; the expressions "pump signal time interval" and "pump signal interval" may also refer to pump signal (time) intervals of equal or non-equal lengths.

A method for generating a shaped laser pulse according to the invention may comprise several preferably consecutive time windows which may or may not have the same lengths. The first time window may have a length of 150 microseconds or less and, in particular, it may have a length of 125 microseconds or less and, in particular, it may have a length of 100 microseconds or less and, in particular, it may have a length of 75 microseconds or less. In the first window the total energy that may be emitted by the pulse may be less than 300 milliJoules (mJ). The energy emitted in the first interval may be less than 30% of the total energy emitted by the laser pulse. In particular, it may be less than 25%, in particular less than 20%, in particular less than 15%, or in particular less than 10% or less than 5% of the total energy emitted by the laser pulse. In particular, the energy emitted in the first window may be less than 200 millliJoules, in particular less than 150 milliJoules, in particular less than 100 milliJoules, and in particular less than 50 milliJoules in some embodiments.

In the second window, the intensity of the pulse may increase and/or remain constant and in a third window the intensity of the laser pulse may decrease again. In particular, the laser pulse may decrease adjustably and/or smoothly and/or quickly in the third window meaning that the decay time during which the laser pulse decreases from its maximum amplitude of intensity to 10% of the maximum intensity amplitude in less than 200 µs, in particular in less than 150 µs, in particular less than 100 µs or in particular less than 50 µs or in considerably shorter time than the pulse duration, in particular in less than half or a fifth or a tenth of the pulse duration. The total time (duration) of the three windows, the duration of the pulse (pulse duration), may be less than 2000 microseconds. In particular, it may be less than 1500 microseconds, in particular less than 1000 microseconds and in particular less than 800 microseconds, in particular less than 600 microseconds and in particular less than 500 microseconds, in particular, less than 400, and in particular in some embodiments less than 300 microseconds. The duration of a pulse may be measured starting from the point wherein 10% of the maximum amplitude of the intensity reached in the whole laser pulse is reached and e.g. ending at a point in time after the maximum amplitude of the intensity has been reached and the pulse has decreased to 10% of the maximum amplitude of the intensity.

Whenever the word amplitude alone is used in this text, it usually refers to the amplitude of the intensity.

The duration of a pulse may be more than 50 microseconds, in particular more than 100 microseconds, and in particular more than 150 microseconds or in particular more than 200 microseconds, and in particular more than 250 microseconds.

In such a pulse, there may be a pre pulse in the first time window, the pre pulse having an amplitude of less than the maximum amplitude of the second and/or third window and/or there may be no pre pulse in the first window. No pre pulse may mean or comprise that the intensity of the shaped pulse increases to its maximum amplitude continuously. In some embodiments, the laser pulse's intensity starts and increases during the first window (at most the first 150 microseconds) from the 10% of the maximum amplitude, which are considered the start of the laser pulse and may not decrease in the first window at all. This increase may be exponential or linear or of any other form in which the intensity amplitude may increase. In other embodiments the laser pulse increases in the first window more quickly and peaks. In that case, the intensity amplitude may decrease again in the first window before it starts to increase again in the second window. A typical duration for a pre pulse would preferably be less than 100 µs. When the amplitude in the first window peaks, the amplitude of that peak may be less than the maximum amplitude of the pulse in the second and/or third window. In particular, it may be less than 80%, in particular, less than 50%, in particular, less than 35%, or in particular less than 20%, in particular less than 10% of the maximal amplitude of the pulse in the second and/or third window.

Such a shaped laser pulse may be generated repetitively. The frequency of the generation of such pulses may be less than 10 kiloHertz (kHz), in particular less than 500 Hertz (Hz) and in particular less than 250 Hertz (Hz), in particular, less than 200 Hertz (Hz), in particular less than 100 Hertz (Hz), in particular, less than 50 Hertz (Hz) and in particular less than 10 Hertz (Hz).

Such a shaped pulse may be particularly useful if used in the field of lithotripsy.

When such a pulse is used in the field of lithotripsy the damage to the calculi may increase with an increasing energy of the pulse. Therefore, the duration of treatment may be reduced by using pulses with higher energy. However, at the same time, for example, care should be taken that not too much energy is applied to a calculus as it might damage the surrounding tissue as well.

The amplitude of the pulse generated by the method described before may be determined e.g. by calculation or adjustment of the laser when it is known what the pulse duration and the total energy of the pulse should be.

The ratio of the maximum amplitude of the intensity of the pulse to the duration of the pulse (pulse duration) may be high. With a high ratio of the maximum amplitude of the intensity of the pulse to the duration of the pulse it is meant in this text that preferably the ratio of the maximum amplitude of the intensity of the pulse to the duration of the pulse for a pulse is above 1 Watt (W) per second(s) per area of the laser beam that is measured perpendicular to the direction of the laser beam and covered by the laser beam (area of the laser beam) or above 5 Watt per second per area of the laser beam or in particular above 10 Watt per second per area of the laser beam or in particular above 50 Watt per second per area of the laser beam, in particular above 500 W/s, in particular more than 5000 W/s, in particular more than 50 000 W/s, in particular more than 500 000 W/s, in particular more than 1 000 000 W/s each time considered per area of the laser beam. A typical area of the laser beam may be less than or about 100 square micrometers ($\mu m)^2$, or less than or about 1000 square micrometers, or less than or about 10 000 square micrometers or less than 1 square millimeters $(mm)^2$ or less than 10 square millimeters, in particular it may be between 10 000 $(\mu m)^2$ and 1 $(mm)^2$.

Alternatively, formulated independent of the area of the laser beam, the ratio of the maximum amplitude of the power of the pulse to the duration of the pulse may be above 1 W/s, in particular more than 5 W/s, in particular more than 10 W/s, in particular more than 50 W/s, in particular more than 5000 W/s, in particular more than 50 000 W/s, in particular more than 500 000 W/s, and in particular more than 1 000 000 W/s.

Shaped pulses may be coupled into a fiber, in particular an optical glass fiber, and may be led to their target through it. For example when used in the field of lithotripsy, the repulsion of a stone may increase with the diameter of such a fiber. Typical diameters of fibers that may be used for pulses shaped according to the method of the invention in a lithotripter as well as for a lithotripter according to the invention may for example be between 200 and 1000 micrometers, in particular they may e.g. be 200 micrometers or 400 micrometers or 600 micrometers or 1000 micrometers.

The monitoring of the pulse shape in the above described methods may in some embodiments be executed by monitoring the total energy of the pulse. This may allow controlling the pulses that are produced by the method e.g. by a feedback loop and sustain the pulse shape after calibration by adjustment of the amplitude of the pump signal.

The energy of a shaped pulse generated according to the method may be more than 1 mJ, in particular more than 10 mJ, in particular more than 25 mJ, in particular more than 100 mJ, in particular more than 500, in particular more than 600 mJ, in particular more than 800 mJ, and in particular more than 1000 mJ, and in particular more than 1300 mJ. Alternatively or additionally it may be less than 5000 mJ, in particular less than 4000 mJ, in particular less than 3500 mJ, in particular less than 2500 mJ, in particular less than 2000 mJ, and in particular less than or more than and/or about 1500 mJ.

The method may be used in a pumped pulsed solid state laser system. It may comprise the step of pumping the laser with a pump signal (which may also be referred to as pumping signal) for generating a pulse of the pumped pulsed solid state laser system, wherein the pump signal comprises several preferably consecutive pump signal time intervals, comprising at least a first pump signal interval, in which the power increases, a second pump signal interval, in which the power remains the same and/or decreases and a third pump signal interval, in which the power increases again.

By this pumping method a pulse may be achieved which has a reduced or a limited or eliminated pre peak pulse compared to state of the art pulses with comparable intensity and/or energy and/or efficiency and/or a longer rise time and/or wherein the latter part of the signal has intensities that are higher than a chosen threshold, for example the disintegration threshold of for example calculi that may be the targets in applications like lithotripsy.

The reduced or limited or eliminated pre peak pulse compared with pulses of state of the art systems with the same maximal pulse intensity amplitude may result from a pumping signal, in which the energy and/or intensity emitted by the pumping signal during the first and/or second pump signal interval is lower than the energy and/or intensity emitted by the pumping signal during or after the third pump signal interval. This may be caused by different maximal intensity amplitudes in those pump signal intervals. It may also be caused by a pumping signal in which the duration of the pumping signal emitted during the first and/or second pump signal interval is smaller than the duration of the pumping intensity emitted during and/or after the third pump signal interval. It may also be caused by a combination of the intensity and the duration of the pump signal intervals of the pumping signal that is adjusted for the particular shaped pulse.

Adjusting the intensity and/or duration of the pumping signal in the first and/or second pump signal interval relative to the intensity and/or duration of and/or after the third pump signal interval may be used to modify the rise time with little or no change in the disintegration part of the pulse. Other embodiments may comprise pumping signals with the same maximum amplitudes in the first and/or second pump signal interval and in and/or after the third pump signal interval.

The aforementioned pump signal may be used to generate a pulse of a pumped pulsed solid state laser system.

In the above described method the pump signal may comprise a fourth pump signal interval in which the power decreases. The decrease in the second and/or fourth pump signal interval may be abrupt and/or adjustable and/or short compared to the pulse duration of the pump signal. An abrupt decrease may mean that the pumping signal falls from the maximum intensity amplitude of the pump signal time interval before (meaning the maximum intensity reached by the pump signal in the pump signal time interval before) to 10% of the maximum amplitude of the time interval before in less than 50 microseconds ($\mu s$), in particular in less than 25 $\mu s$, in particular less than 10 $\mu s$, or in particular less than 1 $\mu s$. Short compared to the pulse duration may mean that the decay time is less than half of the pulse duration, in particular less than a fifth of the pulse duration or in particular less than a tenth of the pulse duration. Whenever a pulse duration is addressed in this text, it particularly may refer to the duration during which the pulse amplitude is equal or higher than ten percent of the maximum pulse amplitude However, a potentially present pre pulse may not be considered when determining the maximum amplitude of a pulse. An adjustment of this decreasing power and/or an abrupt decrease and/or a short decrease in the fourth pump signal interval may in some embodiments have the advantage that the decay shape of the shaped laser pulse may be modified. When a pre pulse is present, a reduction of the amplitude after the pre pulse may not be taken into account, but the duration of the pulse may be measured from the start of the pre pulse to the end of the whole pulse, even if the amplitude may decrease to a lower value than the above referenced criterion in between.

The method described above may be used with a pumped pulsed solid state laser system which has an operation wave length of between 1.0 and 3.0 micrometers ($\mu m$) or in particular of between 1.4 and 2.4 micrometers or of in particular approximately 2.1 micrometers. Such wave lengths may be advantageous as they are in the infra-red region and may be particularly suitable for removal, treatment or ablation of certain types of matter, among them e.g. calculi. In particular, the method for shaping a pulse emitted from a pumped pulsed solid state laser system may for example use a holmium doped yttrium aluminium garnet crystal as lasing material. Such a laser with a holmium doped yttrium aluminium garnet crystal will be referred to as Ho:YAG laser in this text.

A pump signal may comprise two or more pumping pulses. A pumping pulse may also be referred to as pump pulse in this text.

The pump energy of the first pump pulse may be between 1 Joule and 500 Joules. In particular it may be between 10 Joules and 100 Joules and in particular about 50 Joules.

A pumped pulsed solid state laser system may be pumped by a pumping emitter which may be a flash lamp. The pulse shaping in this case may be generated by a power width modulation (PWM) of the flash lamp. Alternatively the amplitude of the pumping signal may be modulated, e.g. by adjusting the current and/or voltage used for the pumping signal. Such a modulation may be chosen in view of the laser pulse generated in the laser thereby. The pumping emitter may also be a diode. The diode may be a laser diode capable of emitting light with the wavelength needed to pump the solid state lasing medium or a slightly smaller wavelength. In other embodiments a pumped pulsed solid state laser system may be pumped by two or more pumping emitters that may comprise two or more flash lamps or two or more diodes or a combination of one or more flash lamps and one or more diodes. As described above, the diodes may be laser diodes capable of emitting light with the wavelength needed to pump the solid state lasing medium or a slightly smaller wavelength. The pumping emitter and/or emitters may pump the system by emitting pulses that may have a certain temporal correlation. For example, a first pumping emitter may start emitting a signal a predetermined time before the second emitter starts to emit a signal. Each pumping emitter may also emit signals with a certain intensity and/or duration and/or energy and/or spectral properties. The intensity and/or duration and/or energy and/or spectral properties of signals that can be emitted by one, two or more pumping emitters in the system may be adjustable or predefined for each pumping emitter separately.

The signals emitted by the pumping emitter or the pumping emitters may comprise or be two or more pulses which may be temporally consecutive to each other and be comprised in separate pump signal time intervals or be comprised in completely or partially overlapping pump signal time intervals.

For every flash lamp that is used, PWM may be used for the pumping signal or signals to influence the resulting pulse shape of the pulse. The first pumping pulse may have a duration of between 50 and 500 microseconds or in particular of between 150 microseconds and 500 microseconds, or of between 100 and 400 microseconds or in particular of between 150 and 350 microseconds. Furthermore, the second pumping pulse may have a duration of between 100 and 2000 microseconds or in particular of between 100 and 1500 microseconds, in particular of between 100 and 1000 microseconds, in particular of between 100 and 800 microseconds, in particular of between 100 and 600 microseconds, in particular of between 100 and 500 microseconds and in particular of between 100 and 400 microseconds or of between 200 and 600 microseconds, or in particular of between 300 and 500 microseconds. The pump signal and/or the first and/or the second pumping pulse may comprise and/or consist of one or more (e.g. equivalent) micropulses. The micropulses may e.g. each have an equal duration and/or intensity as the other micropulses of the pumping signal and/or pumping pulse(s) and/or each or some or all of them may e.g. have a different duration and/or intensity from one or more or all of the other micropulses of the pumping signal and/or pumping pulse(s).

The micropulses may additionally or alternatively have equal and/or different pulse intervals. A pulse interval may mean the interval between the start of a pulse and the start of its consecutive pulse. Thus, in this invention, all of those intervals in one pump signal may be equal, or all of them may be different, or some may be equal to others in the same pump signal and some different.

The second pumping pulse may in some embodiments start between 5 and 400 microseconds or in particular between 50 and 150 microseconds or in particular between 75 and 125 microseconds, in particular between 80 microseconds and 100 microseconds after the first pumping pulse. In particular this may mean that the second pumping pulse starts the described amount of time after the first pumping pulse has decreased to 50% and/or 25% and/or 10% of the maximum amplitude reached by the pulse and/or wherein the second pumping pulse starts the described amount of time after the first pumping pulse having reached the maximum intensity amplitude. In other embodiments it may indicate the time from which the first pumping pulse has reached 10% of the maximum amplitude.

The shaped pulses as described before, which may e.g. be generated in a pumped pulsed solid state laser system may be created with the pumping scheme described before. In the case of a shaped laser pulse having a pre pulse, the pumping pulse in the first and second pump signal interval of the pumping signal may be longer than in a laser pulse in which no pre pulse is created.

The reason for that may be that the pump signal may (heat) add energy to the lasing crystal in the first/second pump signal interval of the pumping signal without reaching the lasing threshold. Thus, the (thermically) prepared crystal may produce a pulse with a reduced or non existing pre peak pulse when pumped with the pump signal of the third pump signal interval. The longer the pumping pulse in the first and/or second pump signal interval of the pump signal is, the higher the energy of the lasing crystal may be. It may therefore be closer to the lasing threshold and/or even reach the lasing threshold.

This may create the (different) pulses that can be emitted by the lasing system of the invention.

In some embodiments using a solid state lasing system the pump pulses have to be adjusted before use in order for the system to generate laser pulses as described before.

The invention further provides a lithotripter comprising a laser system which is configured for emitting a shaped laser pulse wherein, if the pulse duration is divided into four (time) intervals of equal lengths, in the first of those intervals less than 25% of the (total) energy of the whole pulse is emitted. In particular, less than 20%, in particular less than 15%, in particular less than 10% and in particular less than 5% of the complete (total) energy of the pulse may be emitted in the first of four intervals of equal lengths. Furthermore the laser system comprised by such a lithotripter is configured such that the maximum intensity of the pulse is reached for the first time in the second, third or fourth time interval. In particular, it may not be reached in the first time interval. Furthermore, the intensity reached after the start of the third and/or fourth interval is at least once the same as or higher than the maximum intensity reached in the second interval. In particular, the maximum intensity of the pulse may e.g. be reached in the second time interval and remain constant on the maximum of the pulse during the third and in some cases also part of the fourth interval. In other examples the maximum intensity of the pulse may only be reached in the third and/or fourth interval. The expression "at least once" may mean that at least at one time the described intensity is reached.

In particular, the system may be configured for emitting a shaped laser pulse generated by the above-described methods.

Such a lithotripter and/or the laser system may be configured such that a pulse of it may comprise several preferably consecutive time intervals which may have the same lengths. Such time intervals may be the same time intervals as described in the method for generating a shaped pulse before regarding the shaped pulse.

The lithotripter comprising a laser system and/or the laser system may be configured or comprise means to allow execution of one or more of the above-described methods and/or be configured to allow the execution of one or more of the above-described methods.

In particular, such a laser system may be a pumped pulsed solid state laser system for emitting a shaped pulse, in particular a pulse shaped by one of the previously described methods. The system may be configured such that the pulse is shaped by a pump signal comprising several preferably consecutive pump signal time intervals, the pump signal intervals of the pump signal comprising at least a first pump signal interval, in which the power increases, a second pump signal interval, in which the power remains the same and/or decreases and a third pump signal interval, in which the power increases again.

The lithotripter and/or the system may be configured such that it can emit a shaped pulse e.g. as a pulse shaped by the methods described before.

The lithotripter and/or system may for example be configured such that the pump signal may comprise a fourth pump signal interval in which the power decreases. The decrease in the second and/or fourth pump signal interval may be abrupt and/or adjustable and/or short compared to the pulse duration. An abrupt decrease may mean that the (pump) signal falls from the maximum amplitude of the (pump signal) time interval before to 10% of the maximum amplitude of the (pump signal) time interval before in less than 50 microseconds (µs), in particular in less than 25 µs, in particular less than 10 µs, or in particular less than 1 µs. A maximum amplitude of the (pump signal) time interval before may be the maximum amplitude reached in the (pump signal) time interval before. Short compared to the pulse duration may mean that the decay time is less than half of the pulse duration, in particular less than a fifth of the pulse duration or in particular less than a tenth of the pulse duration. The pulse duration may be measured as described before, e.g. between the time when the pulse reaches 10% of the maximum amplitude and the time when the pulse falls to 10% of the maximum amplitude of the pulse.

In the lithotripter and/or system, one or more or all of the steps that have been described before with regard to the method for generating a shaped pulse may be done accordingly. The lithotripter and/or the system may therefore be capable of executing one or more or all of the steps of methods described before and may comprise parts that may be comprised in a lithotripter and/or system that have been described in connection with the method for generating a shaped laser pulse in a lithotripter and wherein the above described method for generating a shaped pulse may be executed.

In addition, the invention provides a method of using shaped pulses of a lithotripter comprising a laser system for lithotripsy. In particular, such a laser system may be a pumped pulsed solid state laser system. In this method the pulses may be shaped according to the above described methods. The invention also provides a method of using a method for generating a shaped laser pulse in a lithotripter for lithotripsy.

These methods may be advantageous. A small vapor bubble which may be created by the methods or in the system or lithotripter described above may when collapsing have less impact on the calculi.

In the two above described methods of using an above described lithotripter and an above described method for generating shaped laser pulses in a lithotripter for lithotripsy, the vapor bubble extending from the fiber to the stone may be completed before the end of the pulse which may be emitted e.g. by a pumped pulsed solid state laser system. In this case before the end of the pulse means that preferably the vapor bubble has been in contact with the stone and freed the path for the laser beam at the latest after two thirds of the duration of the pulse, and/or after one third of the duration of the pulse and/or after one fifth of the duration of the pulse and/or after one tenth of the duration of the pulse. Therefore the energy from the part of the pulse that is emitted by the laser system after the completion of the vapor bubble may be used completely to disintegrate calculi. Its intensity may preferably be above the disintegration threshold of the calculi.

The movement of the calculi at the collapsing of the vapor bubble may be reduced by the above described methods and/or lithotripter and/or laser system creating a bubble with a smooth expansion and a small and longitudinal vapor bubble formation. In addition, the reduced or eliminated pre peak pulse may also influence the vapor bubble to expand smoothly and be of a small formation. Whenever in this text the term pre peak pulse is used, it may refer to the pre peak pulse of state of the art laser systems which this invention may reduce and/or eliminate, whereas the wording pre pulse may refer to the pre pulse present in some embodiments of pulses generated according to the invention.

BRIEF DESCRIPTION OF THE DRAWINGS

Some preferred embodiments are described with reference to the drawings. The drawings comprise.

DETAILED DESCRIPTION OF EXAMPLE EMBODIMENTS

Figure 1:
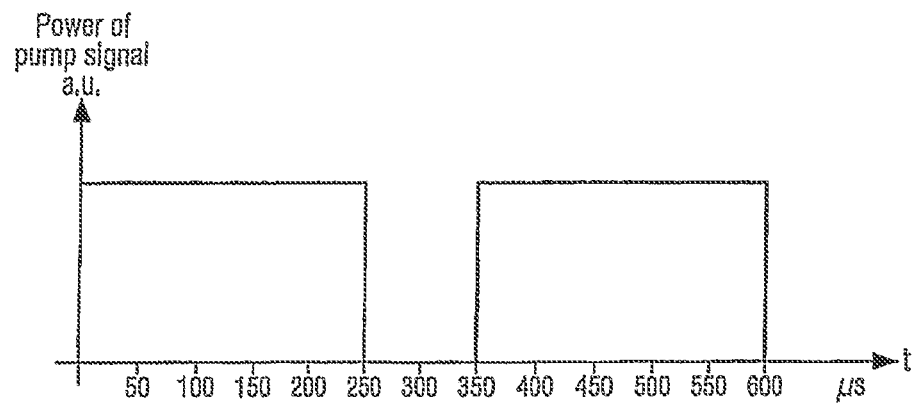
FIG. 1 showing an exemplary example of a pump signal.

FIG. 1 shows an exemplary pump signal, which may be used in combination with a pumped pulsed solid state laser, and in which the first pulse has a duration of 250 microseconds. After a pause interval of 100 microseconds, a second pulse which is in this shown embodiment completely separate from the first pump pulse, is emitted which has a duration of 250 microseconds. Those two pulses together may be used to generate one shaped laser pulse in a laser system and/or lithotripter. In other embodiments, which are not shown here, the two pulses may not be completely separated. In some embodiments the pump signal might be created by pumping using two different pump signals and/or by using two or more partially or completely overlapping or separate pump pulses. This may e.g. be done by using two different pump diodes and/or by using two different flash lamps that may have different spectral properties or the same spectral properties and/or different or the same power and/or by using one diode to pump the system and one flash lamp.

In embodiments comprising diodes, the diodes preferably emit light with a wavelength that has the right energy that is needed to pump the laser system or emit light with little more energy than is needed to pump the laser system. If the energy of the light emitted by the laser diode were smaller than the energy needed to pump the lasing material, no pumping would be achieved. If the energy of the light emitted by the laser diode were much higher than the energy needed to pump the lasing material, the absorption might not be efficient, again possibly inhibiting an efficient pumping of the lasing material.

Figure 2A:
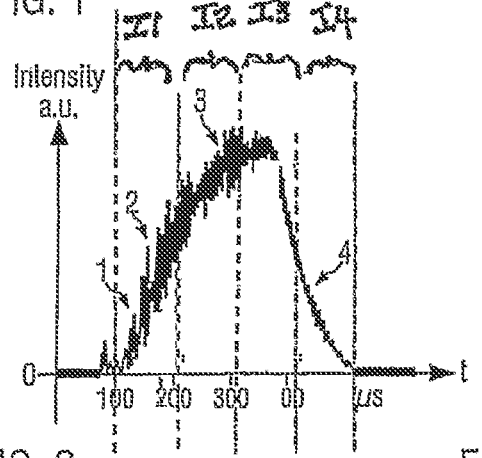
FIGS. 2A-2D showing pulse shapes.

FIG. 2A shows an example of a shaped pulse which may be used for lithotripsy and may have a shape that may be generated by the methods of this invention and/or in the lithotripter of this invention. As can be seen the pulse comprises a small peak pre pulse 1, which is reduced or (nearly) eliminated compared to some state of the art pulses, a rise time 2 during which the vapor bubble may be formed, a disintegration part 3 of the pulse with an intensity that may be used for the disintegration of the stone. In particular, the disintegration part 3 of the pulse may provide the energy needed for disintegration of calculi. Short pulses with a high maximal amplitude may be used. In addition the pulse of FIG. 2A has a short decay time 4 in this embodiment as shown.

The eliminated or at least reduced pre peak pulse and/or the longer rise time of such a shaped pulse may result in a smooth expansion and small vapor bubble formation when used in lithotriptic applications. This means that the way for the beam may be freed and/or that the Moses effect (an expression, which may in this context describe the parting of the water to provide a way to the stone for the laser beam) may be caused with a low energy or at least an energy lower than the energy used in some state of the art systems to create pulses with the same energy and/or intensity and/or efficiency. Investigations with high speed cameras have shown that at a constant distance from the fiber tip to the calculi the time until the vapor bubble is in contact with the calculi is irrespective of the total energy. Therefore, a vapor bubble may be created with a low energy or at least lower energy than necessary in many state of the art systems using pulses with the same maximum intensity and/or efficiency. Once the vapor bubble from the fiber tip to the stone is completed, the vapor bubble is usually not increased by the following part of the pulse. This may be useful as the intensity of that part of the pulse which is not absorbed by the water may then completely be used for calculi ablation. An additional advantage of the smaller bubble is that it induces less stone migration when collapsing.

A short decay time of the pulse may be convenient e.g. if the pulse is to be used for applications like lithotripsy. The decay of the pulse may cause a smooth collapse of the vapor bubble when the system is used in lithotripsy.

Figure 2B:
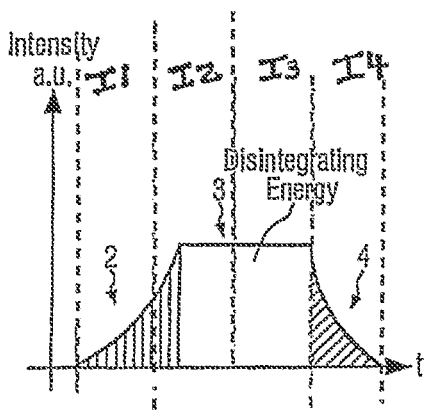

FIG. 2B shows an ideal pulse in an embodiment of the invention which is shaped and may be used in lithotripsy. In region 2 a vapor bubble from fiber tip to stone is prepared when the pulse is used for lithotripsy. The vapor bubble may expand smoothly. This interval 2 is preferably followed by an interval 3 wherein the energy can be used (almost) completely for the disintegration of the stone. This interval is preferably followed by a smooth collapse of the bubble in region 4. In an ideal pulse, there is no pre peak pulse.

It is preferable if the vapor bubble is formed between the fiber tip to the stone e.g. in interval 2 before the maximum or a high intensity is reached as this may lead to minimal energy used for the bubble formation. In addition, if the vapor bubble was not completely formed from fiber tip to the stone, a part of the intensity that could be used for disintegration of the calculi otherwise would be absorbed by the water still in the way between the tip and the stone.

Figure 2C:
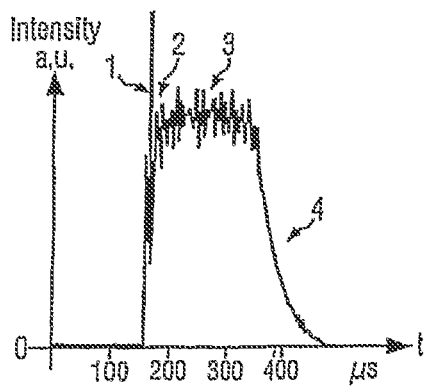

FIG. 2C shows an exemplary pulse usable for lithotripsy in a prior art system. As can be seen, such a pulse emitted by a pumped pulse solid state laser has a very high pre peak pulse 1 which may be several times higher that the laser pulse itself. This solid state laser is pumped by a flash lamp. This pre peak pulse is usually followed by a short rise time 2 with increasing amplitude (which in this case is hardly visible). During the pre peak pulse and the increasing amplitude 2 at the beginning of the pulse a very big and fast growing vapor bubble is created if this pulse is used for lithotripsy. Then the pulse has a plateau 3. As the vapor bubble has not usually met the stone to generate the vapor bubble for the laser beam (Moses effect) when the plateau 3 is reached usually part of the energy of the plateau 3 is absorbed by the water when the pulse is used for lithotripsy. The rest of this energy may then be absorbed by the calculi when used in lithotripsy. The pulse has a decaying part 4 at the end of the pulse during which the vapor bubble collapses. This usually moves the stone away from the fiber tip by a Kelvin Impulse. The larger the vapor bubble is, the higher the Kelvin Impulse may be.

A vapor bubble that is created by the pulse drawn in FIG. 2C is usually big and fast growing as well as fast collapsing and usually leads to much stone movement.

Figure 2D:
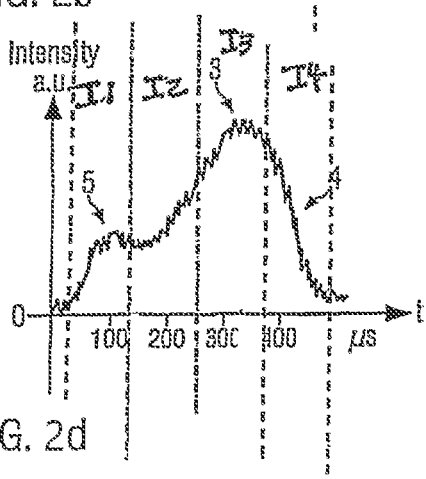

FIG. 2D shows an exemplary pulse according to the invention in which a pre pulse is present. As can be seen a pre pulse 5 with a lower intensity than the main pulse in the interval 3 is present. The main pulse in interval 3 may provide the disintegration energy. This pre pulse 5 may be responsible for forming a small vapor bubble. As the energy comprised in the pre pulse 5 is smaller than the energy of the following rest of the pulse such a bubble may be formed with a low energy or at least an energy lower than the energy used in some state of the art systems. Once the bubble is formed and the way cleared (Moses effect) the remaining intensity of the pulse is not absorbed by water, but can be used almost completely for the disintegration of the stone. The energy of the interval 3 may therefore (nearly) completely be used for the disintegration. The decaying part 4 of the pulse may be such that it causes a smooth collapse of a vapor bubble.

Thus, the system or method according to the invention may be more efficient than a state of the art system or method using the same energy. Furthermore, a smaller bubble may induce less stone migration when collapsing, thereby improving the system or method even further.

Figure 3A:
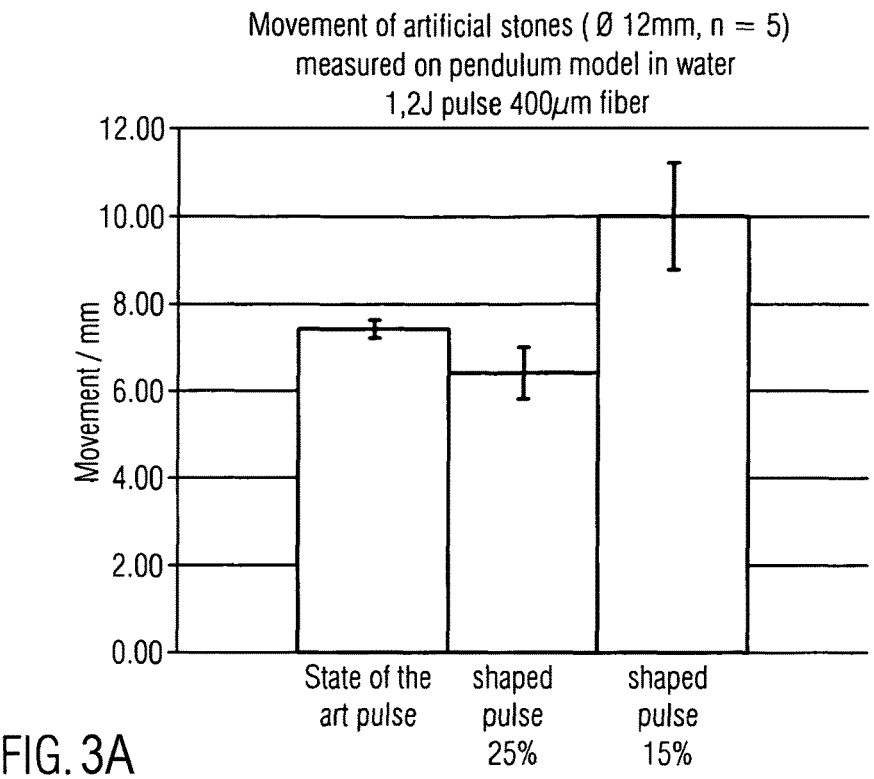
FIGS. 3A and 3B showing the stone movement and the volume reduction on a pendulum model.
Figure 3B:
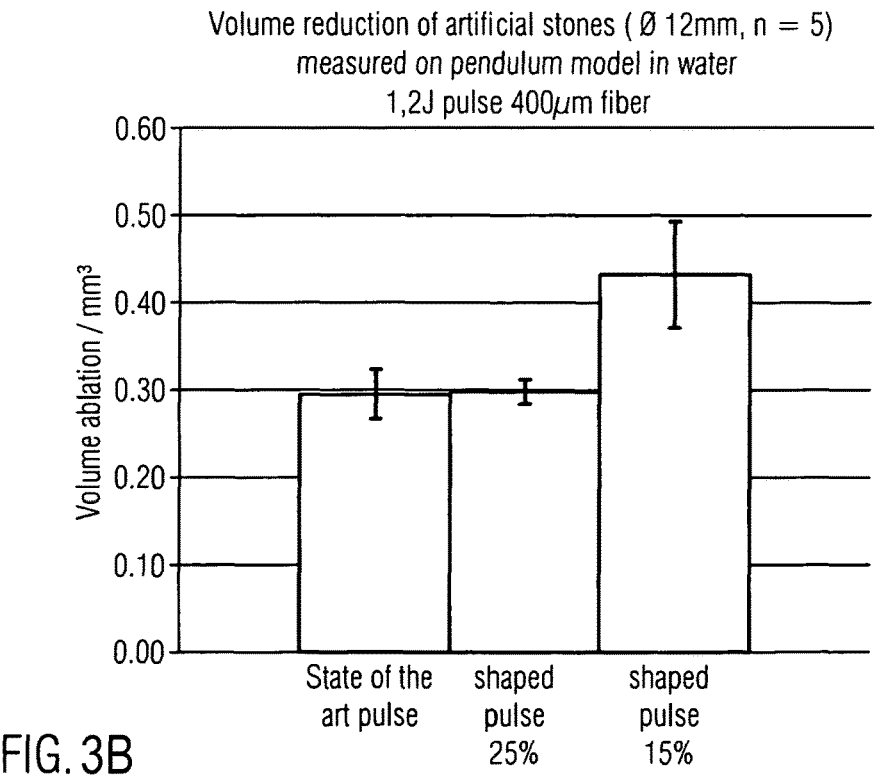

FIG. 3A shows the movement of an artificial stone in water when targeting with a pulse of 1200 miliJoule (mJ) at the distal end of a 400 μm fiber; FIG. 3B the resulted volume reduction of the laser pulses from FIG. 3A when using a state of the art system compared to a system of the invention or a method for generating a shaped laser pulse according to the invention.

In FIG. 3A it can be seen, that a shaped pulse with approx. 25% of the total energy in the first interval shows a significant lower stone movement compared to the state of the art laser pulse. Unlike as published by Kang, according FIG. 3B the stone movement can be reduced without decreasing the volume ablation.

FIG. 3B also shows a possible volume reduction by a shaped pulse of approx. 15% of the total energy in the first pulse interval. By this reduction of the applied energy in the first interval of the shaped pulse compared to the 25% shaped pulse, the volume reduction of the artificial stones can be significantly increased compared to a state of the art pulse when applying equal energy to an artificial stone in water. In FIG. 3A the resulting stone movement of the approx. 15% shaped pulses is shown. The significant higher stone movement of the 15% shaped laser pulse may be the result of the significant higher ablation volume which increases also the momentum due to the plume ejected from the stone.

These different pulse shapes of the invention can improve and accelerate the treatments of calculi in living beings. Pulse shapes with high efficient ablation could be used in cases with low stone migration e.g. at bigger calculi or if the calculi is embedded in tissue or in the kidney because there is less space for movement, or if a basket is used to prevent the movement of the calculi.

Pulse shapes which results in lower stone movement but equal ablation efficiency compared to the state of the art could be used for the smaller calculi or fragments and if the migration is a problem e.g. in the ureter.

A typical shaped laser pulse generated according to the method of the invention and/or in lithotripter and/or laser system according to the invention comprises in the first of four time intervals of equal length less than 20% of the energy of the pulse.

In a first time window which may have a length of 100 µs or less and/or in a first time interval having a duration of 25% of the pulse duration, less than 20% of the total pulse energy may be emitted. The shaped laser pulse may have a duration of between 200 µs and 500 µs and may have a pre pulse with an amplitude of less 50% of the maximum amplitude reached in the second or third time window.

The total energy of such a pulse may be more than 500 mJ and/or less than 4000 mJ.

A typical pump signal for generating a shaped laser pulse may comprise two pumping pulses. The first pumping pulse may have a duration of between 150 µs and 500 µs. The second pumping pulse may have a duration of between 100 µs and 500 µs and may start between 80 µs and 100 µs after the first pumping pulse.

A typical lithotripter comprising a laser system may be configured for emitting a shaped laser pulse according to the above described method and/or comprise means for allowing execution of the above identified methods, in particular the methods with the above described parameters.

The invention claimed is:

1. A method for generating a shaped laser pulse in a lithotripter, the method comprising:
generating the shaped laser pulse using a pumped pulsed solid state laser system comprising a pumping emitter controlled to emit a light having a wavelength to pump a lasing medium to generate the shaped laser pulse, the shaped laser pulse having a pulse duration that has four consecutive intervals of equal lengths that make up the pulse duration, wherein less than 25% of the energy of the shaped laser pulse is emitted in the first interval of the four intervals, and a maximum intensity of the shaped laser pulse is first reached after the first interval of the four intervals, wherein an intensity of the shaped laser pulse reached after the start of the third interval is at least once not lower than a maximum intensity of the shaped laser pulse reached in the second interval, wherein the pulse duration of the shaped laser pulse is more than 50 microseconds, and wherein the energy of the shaped laser pulse is more than 500 mJ.

2. The method according to claim 1, wherein a ratio of a maximal amplitude of the shaped laser pulse to the pulse duration is higher than 1 W/s per area of the laser beam.

3. The method according to claim 1, wherein the pulse shape of the shaped laser pulse is monitored by monitoring the total energy of the pulse and/or wherein the total energy of the pulse is more than 1 mJ and/or less than 5000 mJ.

4. The method according to claim 1, wherein the intensity of the shaped laser pulse reached after the start of the third interval is reached after the start of the fourth interval.

5. The method according to claim 4, wherein an intensity of the shaped laser pulse reached after the start of the third interval is at least once the same as the maximum intensity of shaped laser pulse reached in the second interval.

6. The method according to claim 4, wherein an intensity of the shaped laser pulse reached after the start of the third interval is at least once higher than the maximum intensity of shaped laser pulse reached in the second interval.

7. The method according to claim 1, wherein the pumping emitter comprises a diode.

\* \* \* \* \*